United States Patent
Gupta et al.

(10) Patent No.: US 11,202,893 B2
(45) Date of Patent: Dec. 21, 2021

(54) BRAIDED DRAINAGE CATHETER

(71) Applicant: BOSTON SCIENTIFIC SCIMED, INC., Maple Grove, MN (US)

(72) Inventors: Ajay Gupta, Shoreview, MN (US); Timothy Lawrence Rubesch, Blaine, MN (US); Mark Steven Smith, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 543 days.

(21) Appl. No.: 16/172,009

(22) Filed: Oct. 26, 2018

(65) Prior Publication Data
US 2019/0126016 A1 May 2, 2019

Related U.S. Application Data

(60) Provisional application No. 62/577,799, filed on Oct. 27, 2017.

(51) Int. Cl.
*A61M 27/00* (2006.01)
*A61M 25/00* (2006.01)
(Continued)

(52) U.S. Cl.
CPC ........ *A61M 27/002* (2013.01); *A61M 25/005* (2013.01); *A61M 25/0012* (2013.01);
(Continued)

(58) Field of Classification Search
CPC ............ A61M 27/002; A61M 25/0012; A61M 25/005; A61M 25/0053; A61M 25/007;
(Continued)

(56) References Cited

U.S. PATENT DOCUMENTS 286,718 A 10/1883 Linton
1,221,118 A 4/1917 Ward
(Continued)

FOREIGN PATENT DOCUMENTS

EP 2316518 A1 5/2011
GB 411298 A 6/1934
(Continued)

OTHER PUBLICATIONS

International Search Report and Written Opinion dated Feb. 13, 2019 for International Application No. PCT/US2018/048488.

*Primary Examiner* — Adam Marcetich
(74) *Attorney, Agent, or Firm* — Seager, Tufte & Wickhem, LLP

(57) ABSTRACT

A drainage catheter may include a polymeric tubular member and a braided reinforcement that is disposed about the polymeric tubular member. The braided reinforcement may include a repeating braid pattern that extends over a first portion of a length of the drainage catheter and a modified braid pattern that extends over a second portion of the length of the drainage catheter, the modified braid pattern providing a region without any braid filaments. The drainage catheter may include a drainage hole that extends through the polymeric tubular member within the region without any braid filaments.

22 Claims, 11 Drawing Sheets

(51) Int. Cl.
  *B29C 53/14* (2006.01)
  *B29L 31/00* (2006.01)
(52) U.S. Cl.
  CPC .......... *B29C 53/14* (2013.01); *A61M 25/007* (2013.01); *A61M 25/0053* (2013.01); *A61M 2205/32* (2013.01); *A61M 2207/00* (2013.01); *B29L 2031/7542* (2013.01)
(58) Field of Classification Search
  CPC .......... A61M 2205/32; A61M 2207/00; B29L 2031/7542
  See application file for complete search history.

(56) References Cited

U.S. PATENT DOCUMENTS

| | | | |
|---|---|---|---|
| 2,064,218 | A | 12/1936 | Richardson |
| 2,134,987 | A | 11/1938 | Shorb |
| 2,931,597 | A | 4/1960 | Moore, Jr. |
| 3,683,530 | A | 8/1972 | Robinson |
| 5,462,523 | A * | 10/1995 | Samson ............ A61M 25/0043 604/246 |
| 5,755,405 | A | 5/1998 | Socha et al. |
| 5,782,811 | A | 7/1998 | Samson et al. |
| 6,152,911 | A * | 11/2000 | Giannoble ........ A61M 25/0026 604/264 |
| 6,182,924 | B1 | 2/2001 | Nott |
| 6,945,956 | B2 | 9/2005 | Waldhauser et al. |
| 9,108,017 | B2 | 8/2015 | Pingleton et al. |
| 2003/0078564 | A1* | 4/2003 | Viitala ................ A61M 60/857 604/540 |
| 2004/0122360 | A1* | 6/2004 | Waldhauser ........ A61M 25/005 604/95.04 |
| 2005/0049575 | A1 | 3/2005 | Snell et al. |
| 2005/0192558 | A1 | 9/2005 | Bernard et al. |
| 2008/0262472 | A1* | 10/2008 | Lunn ................ A61M 25/0012 604/527 |
| 2009/0076482 | A1* | 3/2009 | Jonkman ............. A61M 25/005 604/526 |
| 2010/0114070 | A1* | 5/2010 | Wilson ................ A61M 25/005 604/524 |
| 2012/0035586 | A1* | 2/2012 | O'Day .............. A61M 25/0043 604/508 |
| 2012/0241076 | A1* | 9/2012 | Pingleton ................ B29C 53/60 156/64 |
| 2013/0018318 | A1* | 1/2013 | Ravichandran ... A61M 25/0012 604/172 |
| 2014/0046301 | A1* | 2/2014 | Kuwada ............ A61M 25/0012 604/527 |
| 2015/0174363 | A1* | 6/2015 | Sutermeister ...... A61M 25/0054 604/95.04 |
| 2017/0021127 | A1* | 1/2017 | Manouchehr ....... A61M 25/005 |
| 2017/0072166 | A1* | 3/2017 | Hiroshige ......... A61M 25/0051 |
| 2017/0080178 | A1* | 3/2017 | O'Connell ............ A61M 25/01 |

FOREIGN PATENT DOCUMENTS

| | | |
|---|---|---|
| GB | 456076 A | 11/1936 |
| GB | 463196 A | 3/1937 |
| GB | 485599 A | 5/1938 |
| WO | 0113984 A2 | 3/2001 |
| ZA | 970020 A | 1/1997 |

* cited by examiner

BRAIDED DRAINAGE CATHETER

CROSS-REFERENCE TO RELATED APPLICATIONS

This application claims the benefit of priority under 35 U.S.C. § 119 to U.S. Provisional Application Ser. No. 62/577,799, filed Oct. 27, 2017, the entirety of which is incorporated herein by reference.

TECHNICAL FIELD

The present disclosure pertains to medical devices, and methods for manufacturing medical devices. More particularly, the present disclosure pertains to catheters including drainage catheters that are braided.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a catheter having an inner polymeric layer and a braided reinforcement that is disposed about the inner polymeric layer. The catheter includes a first portion in which the braided reinforcement has a first filament pattern and a second portion in which the braided reinforcement has a second filament pattern different from the first filament pattern. An outer polymeric layer is disposed about the braided reinforcement and includes an outer surface. One or more drainage holes extend through the inner polymeric layer and the outer polymeric layer and are disposed within the second portion of the catheter.

Alternatively or additionally, the second filament pattern may be configured to enable the one or more drainage holes to pass through the braided reinforcement without cutting or breaking any of the filaments forming the braided reinforcement.

Alternatively or additionally, the one or more drainage holes may be disposed relative to the braided reinforcement such that each of the filaments extend intact from a position distal of the one or more drainage holes to a position proximal of the one or more drainage holes.

Alternatively or additionally, the reinforcement braid may be configured such that the second filament pattern of the reinforcement braid provides a region free of filaments in order to accommodate the one or more drainage holes.

Alternatively or additionally, the reinforcement braid may be braided to include the region free of filaments.

Alternatively or additionally, the reinforcement braid may include metal filaments.

Alternatively or additionally, the reinforcement braid may include polymeric filaments.

Alternatively or additionally, the first filament pattern may provide a uniform spacing between braid filaments.

Alternatively or additionally, the second filament pattern may provide a non-uniform spacing between braid filaments.

Another example medical device is a drainage catheter that includes a polymeric tubular member and a braided reinforcement that is disposed about the polymeric tubular member and that includes a repeating braid pattern extending over a first portion of a length of the drainage catheter. The braided reinforcement includes a modified braid pattern extending over a second portion of the length of the drainage catheter, the modified braid pattern providing a region without any braid filaments. A drainage hole extends through the polymeric tubular member and is disposed within the region without any braid filaments.

Alternatively or additionally, the drainage catheter may further include a polymeric sheath that is disposed over the braided reinforcement, with the drainage hole extending through the polymeric sheath.

Alternatively or additionally, the modified braid pattern may extend over less than about 25 percent of the length of the drainage catheter.

Alternatively or additionally, the modified braid pattern may extend over less than about 10 percent of the length of the drainage catheter.

Alternatively or additionally, the braided reinforcement may include stainless steel and/or tungsten.

Alternatively or additionally, the braided reinforcement may include polyetheretherketone (PEEK) or high molecular weight polyethylene.

Alternatively or additionally, the braided reinforcement may include a hybrid of metal filaments and polymer filaments.

A method of forming a medical device includes a method of forming a drainage catheter including a braided reinforcement and a drainage hole. The method includes braiding a braided reinforcement over a polymeric inner liner. The braided reinforcement includes a repeating braid pattern extending over a first portion of a length of the drainage catheter and a modified braid pattern extending over a second portion of the length of the drainage catheter, the modified braid pattern providing a region without any braid filaments. A polymeric outer sheath is reflowed over the braided reinforcement. A drainage hole that extends through the polymeric inner liner and the polymeric outer sheath is formed, the drainage hole positioned within the region without any braid filaments.

Alternatively or additionally, forming the drainage hole may not damage any of the braid filaments of the braided reinforcement.

Alternatively or additionally, forming the drainage hole may include drilling, milling, hole-punching, laser cutting or melting through the polymeric inner liner and the polymeric outer sheath.

Alternatively or additionally, braiding the braided reinforcement may include programming a braiding machine to produce the repeating braid pattern extending over a first portion of a length of the drainage catheter and a modified braid pattern extending over a second portion of the length of the drainage catheter.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
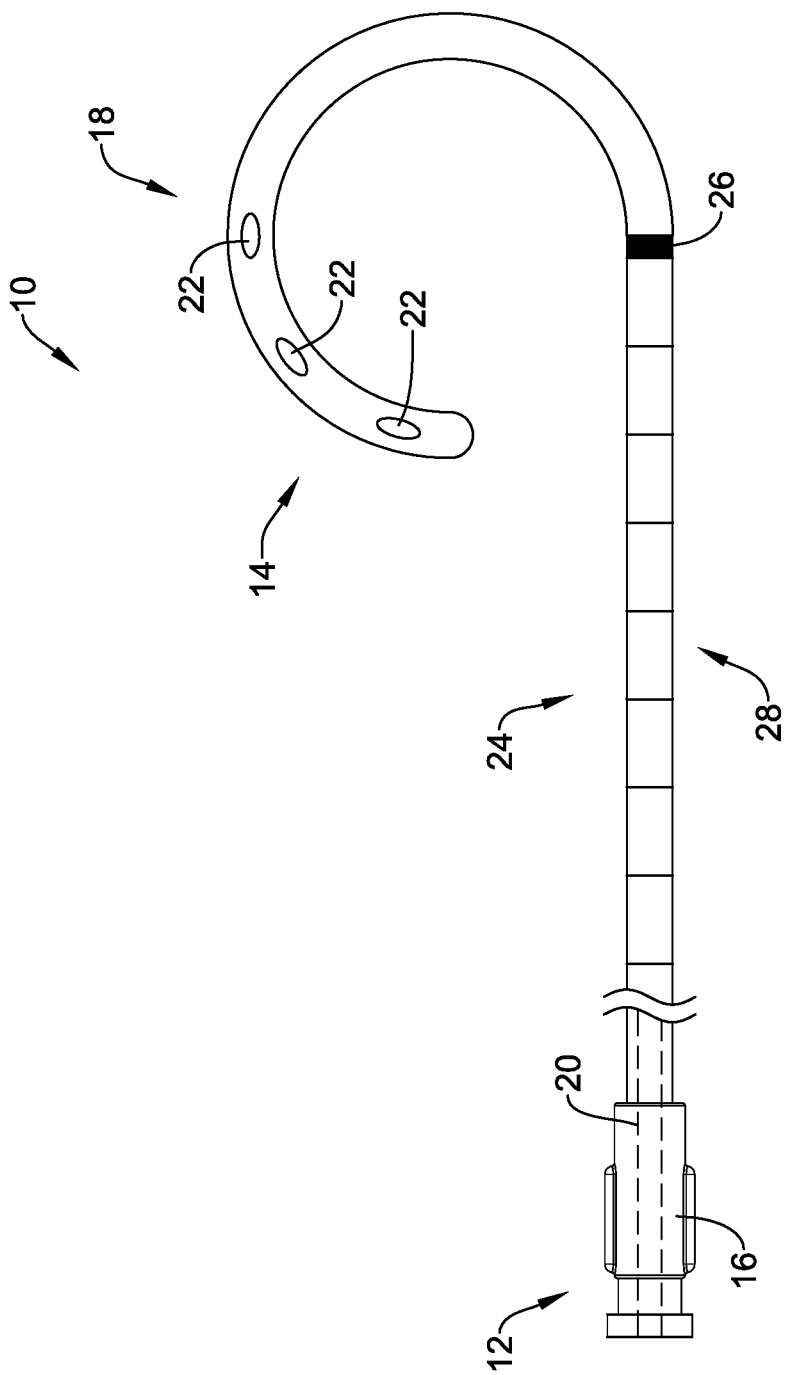
FIG. 1 is a schematic diagram of a drainage catheter in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Drainage catheters are used in a variety of different applications in which there is a desire to remove a fluid from within the human body. In some cases, a drainage catheter may be used in applications in which there is a desire to remove a fluid from within a particular organ or other structure within the human body. FIG. 1 is a schematic illustration of a drainage catheter 10. In some cases, as shown, the drainage catheter 10 extends from a proximal region 12 to a distal region 14. As illustrated, the drainage catheter 10 includes a hub 16 disposed within the proximal region 12. The hub 16 may, for example, include a luer fitting that enables connection of the hub 16 to additional tubing for drainage, or perhaps to a source of vacuum to facilitate drainage. The drainage catheter 10 includes a lumen 20, shown in phantom extending through the hub 16.

In the distal region 14, the drainage catheter 10 may in some cases include a curved portion 18. While the curved portion 18 is illustrated as curving within a single plane (within the page of the drawing), it will be appreciated that in some cases the curved portion 18 may additionally curve in a second plane orthogonal to the page of the drawing, and thus may curve either out of the page (towards the viewer) or into the page (away from the viewer). These are just examples. In some cases, the drainage catheter 10 may include a mechanism such as an internal pull mechanism in order to change the curvature of the curved portion 18. In some instances, such an internal pull mechanism may also help to stabilize the shape of the curved portion 18. In some cases, inclusion of a braid within the drainage catheter 10, as will be discussed, may permit the curved portion 18 to retain its shape without any additional mechanism. In some cases, the shape of the curved portion 18 may be heat set.

Figure 2:
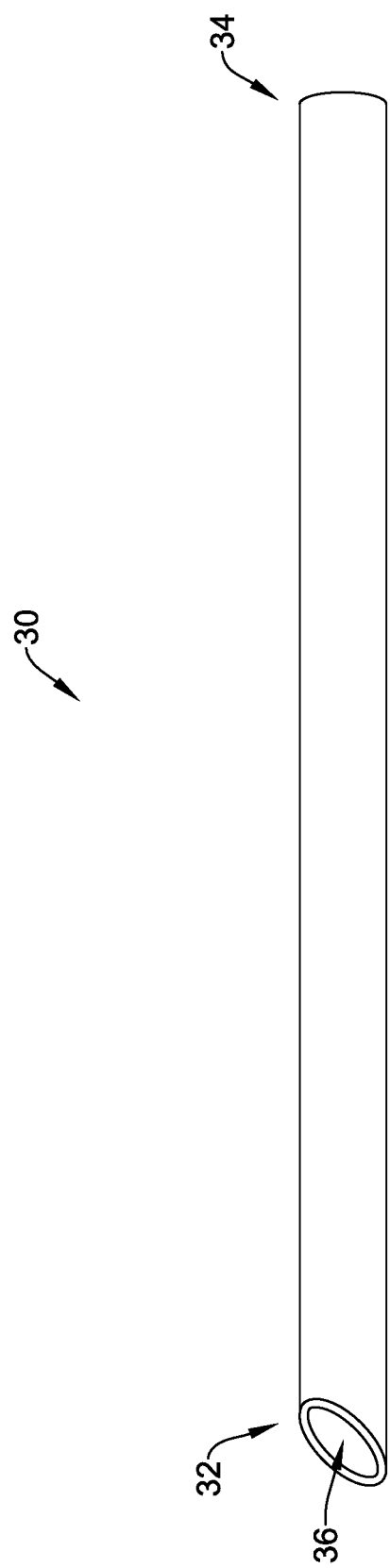
FIG. 2 is a schematic view of a polymeric inner member forming a portion of the drainage catheter of FIG. 1.
Figure 3:
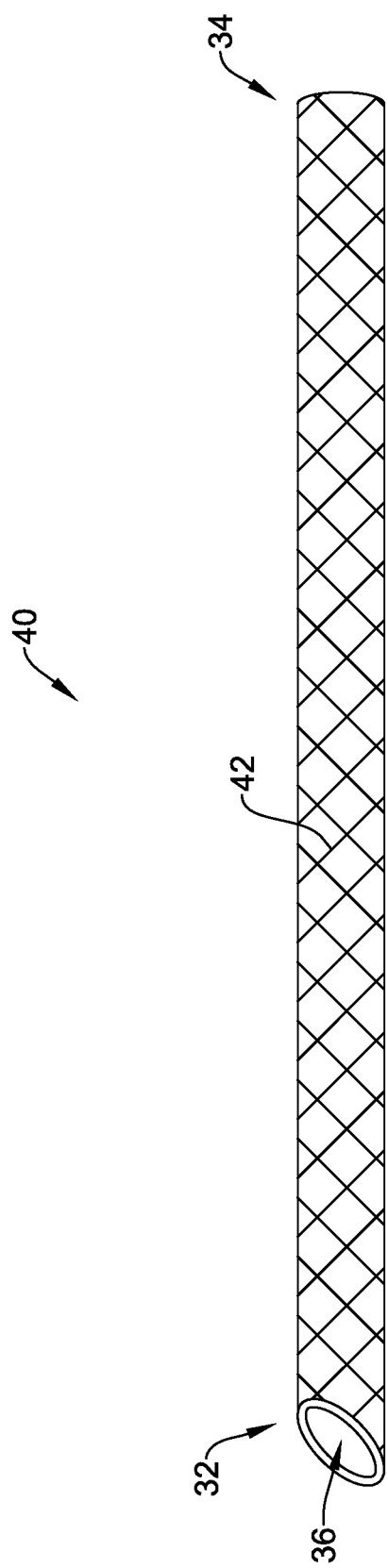
FIG. 3 is a schematic view of an assembly including a braided reinforcement disposed over the polymeric inner member of FIG. 2 in accordance with an example of the disclosure.
Figure 4:
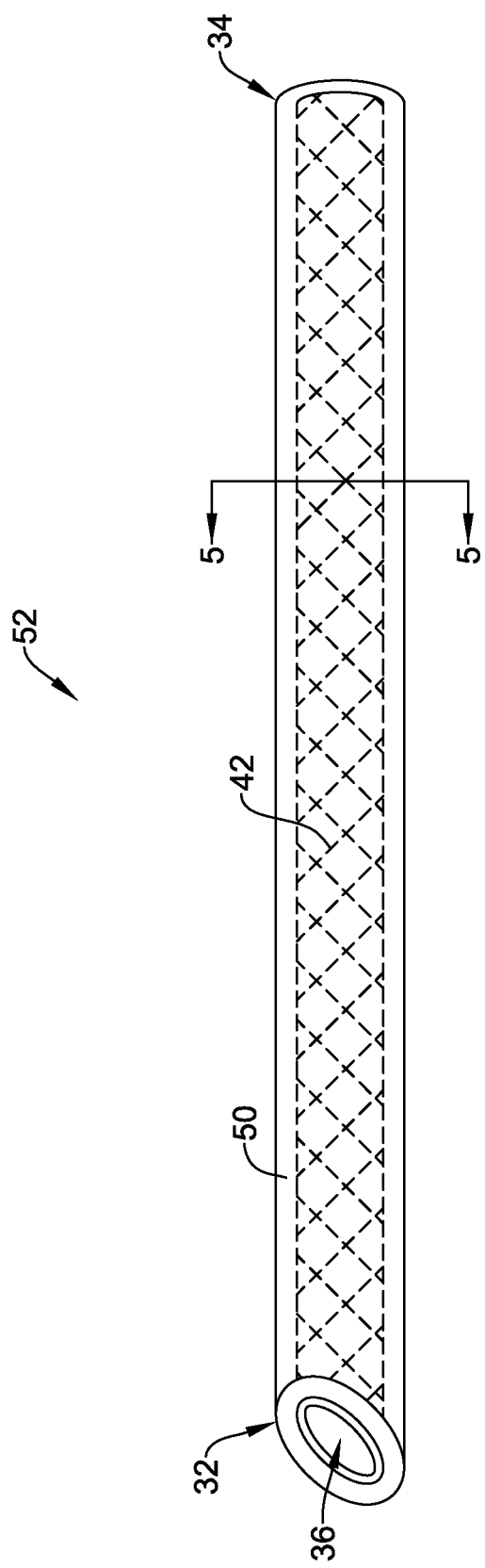
FIG. 4 is a schematic view of an assembly including a polymeric outer sheath disposed over the assembly of FIG. 3 in accordance with an example of the disclosure.

The distal region 14 includes several drainage holes 22 that extend into and are in fluid communication with the lumen 20. In some cases, the drainage holes 22 may be aligned along the distal region 14. In some instances, the drainage holes 22 may be radially spaced apart around the distal region 14. In some cases, for example, this may mean that regardless of the use orientation of the drainage catheter 10 relative to the fluid source within the human body, one or more of the drainage holes 22 may face up, one or more of the drainage holes 22 may face down, several may face sideways, and so on. In some cases, one or more of the drainage holes 22 may vary in diameter in order to accommodate desired drainage rates. The drainage catheter 10 includes an intermediate portion 24 that extends between the proximal region 12 and the distal region 14. In some cases, the intermediate portion 24 may include one or more marker bands 26, although only a single marker band 26 is illustrated. The one or more marker bands 26, if present, may be formed of a radiopaque material such as tungsten and may assist the technician deploying the drainage catheter 10 in properly placing the drainage catheter 10 under fluoroscopy. In some instances, the drainage catheter 10 may also include a plurality of length markers 28, again, to facilitate appropriate placement of the drainage catheter 10. In some cases, the drainage catheter 10 may be formed having multiple layers. FIG. 2 through FIG. 4 are schematic illustrations of members forming a portion of the drainage catheter 10.

FIG. 2 shows a polymeric inner member 30 that extends from a proximal end 32 to a distal end 34 and that defines a lumen 36. It will be appreciated that the lumen 36 may be considered as being representative of the lumen 20 shown in FIG. 1. The polymeric inner member 30 may be formed of any suitable polymeric material, including polymeric materials that have relatively higher melting points, are chemically resistant, are flexible yet kink-resistant, are formable, and are impervious to fluids. Suitable polymers include fluoropolymers such as but not limited to polytetrafluoroethylene (PTFE), polyolefins such as but not limited to crosslinked polyethylene, polyurethanes, Nylon®, silicone, EVA (ethylene vinyl acetate), PVC (polyvinyl chloride) and copolymers and blends thereof.

FIG. 3 shows an assembly 40 that includes a braided reinforcement 42 that has been braided over the polymeric inner member 30. While the braid pattern shown in FIG. 3 is uniform and repeating, this is merely illustrative. In some cases, as will be discussed, the braid pattern of the braided reinforcement 42 may have multiple patterns in order to accommodate formation of the drainage holes 22 (FIG. 1) without having to cut or otherwise damage the braided reinforcement 42. In some cases, this can reduce the possible risk of corrosion, as the braided reinforcement 42 is not exposed to tissue or bodily fluids. In some cases, the braided reinforcement 42 may have a first pattern that extends over a substantial fraction of the braided reinforcement 42 and a second pattern that corresponds to where the drainage holes 22 are to be formed. In some cases, the first pattern may be uniform over a length of the braided reinforcement 42. In some instances, portions of the first pattern may vary to provide desired flexibility, stiffness, radiopacity and formability characteristics. In some cases, portions of the first pattern may vary in braid density (crossings per inch), or the filament patterns themselves may vary.

Figure 5:
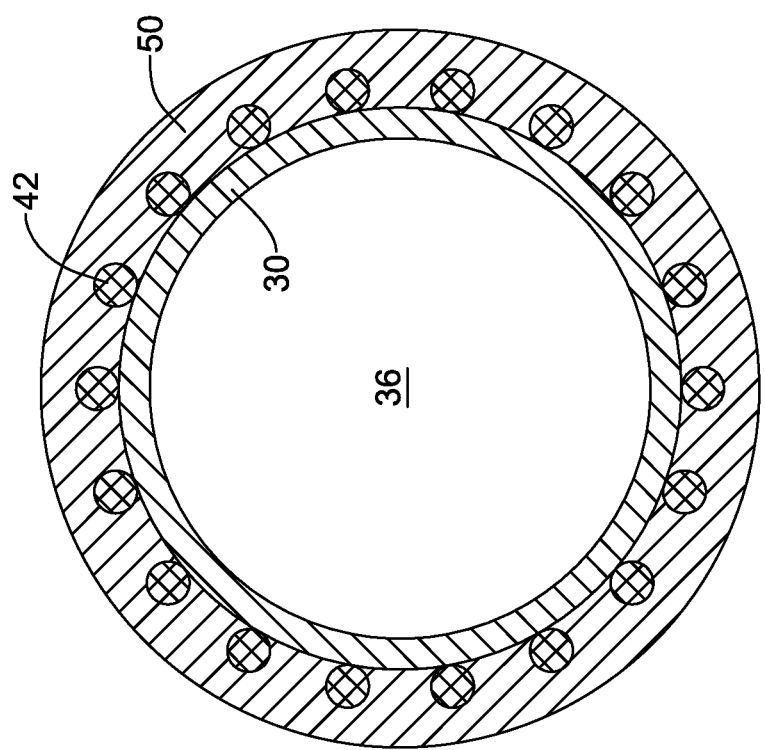
FIG. 5 is a cross-sectional view of the assembly of FIG. 4, taken along the line 5-5.

Once the braided reinforcement 42 has been formed, thereby forming the assembly 40, a polymeric outer sheath 50 may be disposed over the braided reinforcement 42, thereby forming an assembly 52 as seen in FIG. 4. In some cases, the polymeric outer sheath 50 may be made from a single polymeric material, having a single durometer value over the length of the polymeric outer sheath 50. In some instances, the polymeric outer sheath 50 may be made of multiple durometer materials at varying lengths. In some cases, the braided reinforcement 42 may become at least partially embedded within the polymeric outer sheath 50, particularly if the polymeric outer sheath 50 is reflowed onto the assembly 40. This can be seen for example in FIG. 5, which is a cross-sectional view of the assembly 52.

Figure 6:
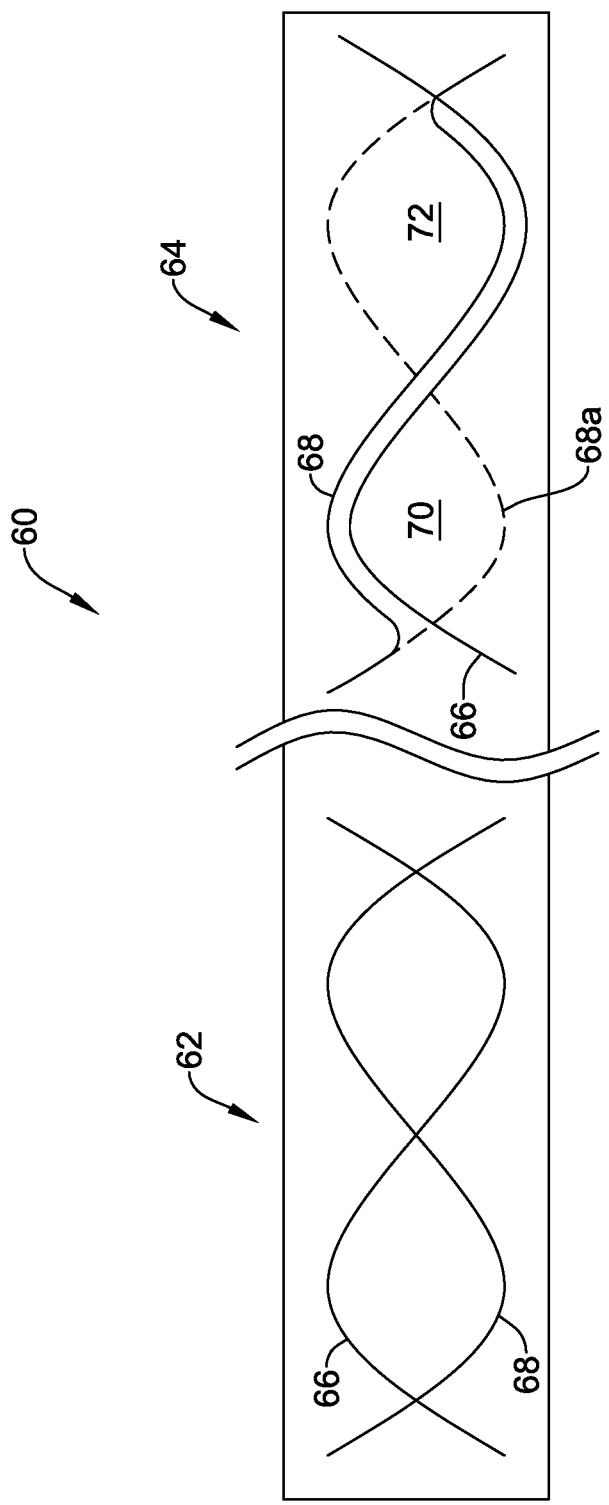
FIG. 6 is a schematic illustration of a portion of a catheter including a first braid profile and a second braid profile in accordance with an example of the disclosure.

As noted, in some cases, the braided reinforcement may be configured to accommodate the drainage holes 22. FIG. 6 is a simplified example of a catheter shaft 60 that may for example be considered as being representative of a portion of the drainage catheter 10. The catheter shaft 60 includes a first portion 62 having a first braid pattern and a second portion 64 having a second braid pattern that is different from the first braid pattern. The first portion 62 includes a first filament 66 and a second filament 68 that may be seen as forming a helical pattern. It will be appreciated that this helical pattern is merely illustrative, and should be considered as being a substantial simplification of an actual braid pattern such as might be present in the braided reinforcement 42 (FIG. 3). In some cases, for example, the catheter shaft 60 may include linear filaments, particularly in portions of the catheter shaft 60 that will not include drainage holes. In the second portion 64, while the first filament 66 has a similar orientation to that shown in the first portion 62, the second filament 68 has been moved. The relative position of the second filament 68 (in the first portion 62) is shown in the second portion 64 as a dashed line 68a. As a result of changing the position of the second filament 68 relative to the first filament 66, it can be seen that a void 70 and a void 72 is formed in which no filament is present. Accordingly, these voids 70, 72 provide examples of where drainage holes 22 (FIG. 1) may be drilled, milled, laser cut or otherwise formed without damaging the filaments.

In some cases, the modified braid pattern, as seen in the second portion 64, may extend over less than about 25 percent of the length of the drainage catheter 10. In some cases, the modified braid pattern may extend over less than about 10 percent of the length of the drainage catheter 10. In some cases, the filaments 66, 68 may be made of stainless steel or tungsten. In some instances, the filaments 66, 68 may be made of PEEK (polyetheretherketone) or high molecular weight polyethylene.

Figure 7:
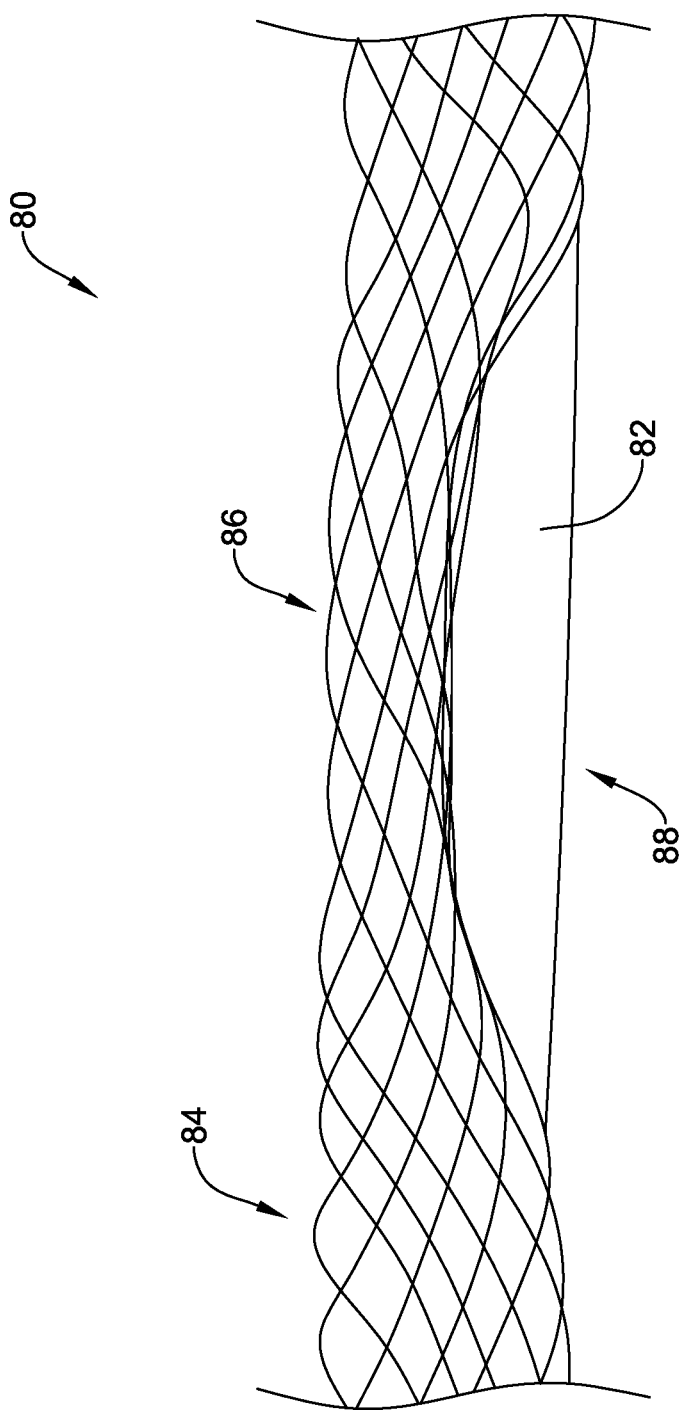
FIG. 7 is a side view of a braided reinforcement in accordance with an example of the disclosure.

FIG. 7 provides another example. FIG. 7 shows a braided reinforcement 80 that has been braided (for illustrative purposes) over a mandrel 82. The braided reinforcement 80 includes a first portion 84 in which the individual filaments can be seen as being braided in a uniform, repeating pattern. The braided reinforcement 80 also includes a second portion 86 in which the individual filaments are not braided in a uniform, repeating pattern, and instead have been moved to one side (upward in the illustrated orientation) to form a void 88. As will be appreciated, the change in braiding pattern shown in FIG. 7 may be relatively extreme, but does show how the braiding pattern may be altered in order to provide voids through which drainage holes 22 may be formed. In some cases, the braided reinforcements 42, 80 may be formed using a braiding machine. In some instances, a braiding machine may be programmed to provide a uniform, repeating pattern where desired and a non-uniform pattern where required. In some cases, braiding machines such as those available commercially under the HERZOG® name may be used. As a result, it is possible to form drainage catheters that are braid-reinforced, thereby providing drainage catheters with improved properties such as kink resistance and pushability while simultaneously enjoying relatively reduced wall thicknesses. This can mean a stronger catheter for a given diameter, or a smaller diameter catheter for a given kink resistance and pushability. This can mean a smaller outer diameter for a given lumen size, or a larger lumen size for a given outer diameter, for example.

Figure 8:
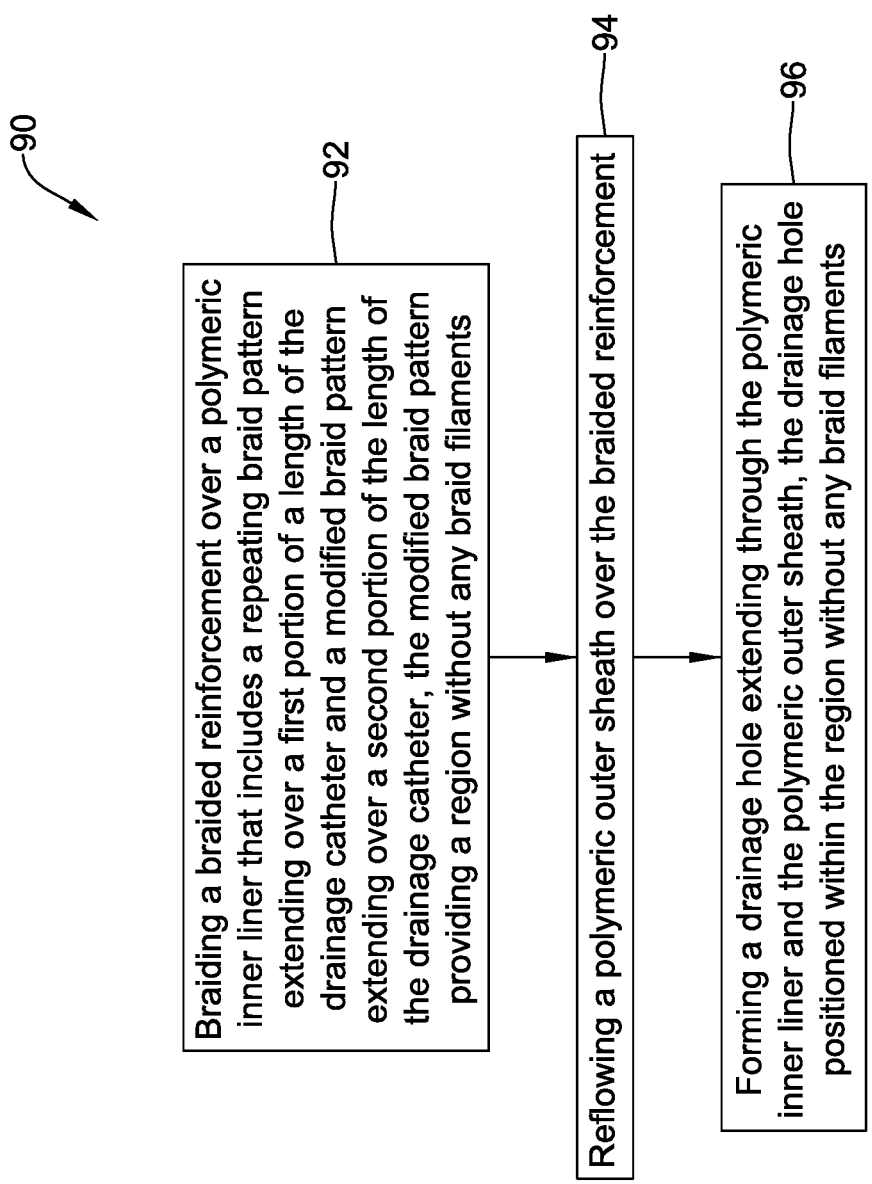
FIG. 8 is a flow diagram showing a method of forming a drainage catheter in accordance with an example of the disclosure.

FIG. 8 is a flow diagram showing a method 90 of forming a drainage catheter such as the drainage catheter 10 shown in FIG. 1. The method 90 begins braiding a braided reinforcement over a polymeric inner liner, as generally indicated at block 92. In some cases, the braided reinforcement includes a repeating braid pattern that extends over a first portion of a length of the drainage catheter and a modified braid pattern that extends over a second portion of the length of the drainage catheter, the modified braid pattern providing a region without any braid filaments. In some cases, this includes programming a braiding machine to provide these braid patterns. A polymeric outer sheath may be reflowed over the braided reinforcement, as seen at block 94. Drainage holes may be formed that extends through the polymeric inner liner and the polymeric outer sheath, the drainage holes positioned within the region without any braid filaments, as generally indicated at block 96. In some cases, forming the drainage holes does not damage any of the braid filaments of the braided reinforcement. In some instances, forming the drainage holes includes drilling, milling, hole-punching, laser cutting or melting through the polymeric inner liner and the polymeric outer sheath.

Figure 9:
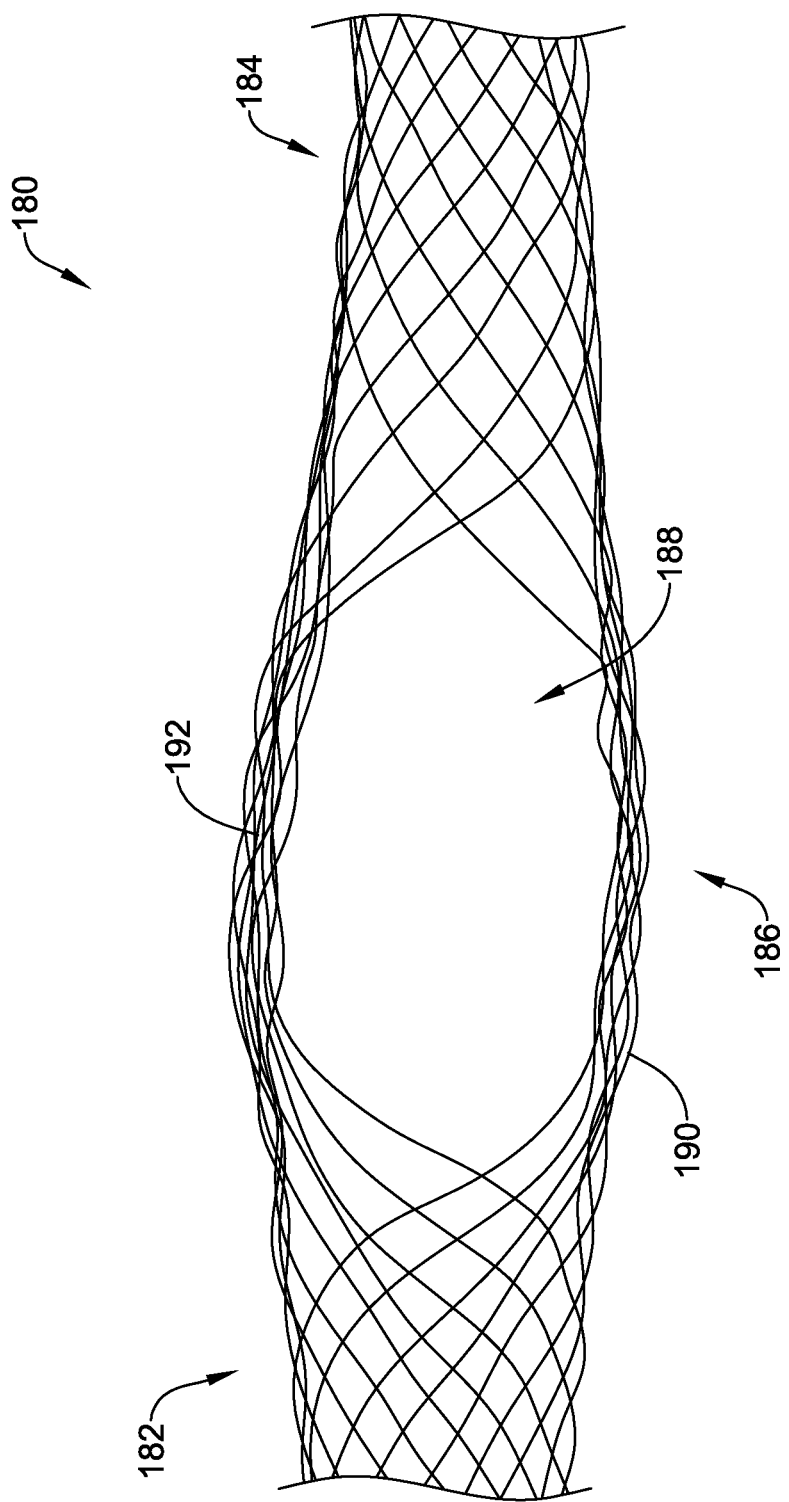
FIG. 9 is a side view of a braided reinforcement in accordance with an example of the disclosure.

FIG. 9 provides another example of a braided reinforcement 180. The braided reinforcement 180 includes a first portion 182 in which the individual filaments can be seen as being braided in a uniform, repeating pattern, and a second portion 184 in which the individual filaments can be seen as being braided in a uniform, repeating pattern. In some instances, the first portion 182 and the second portion 184 have the same uniform, repeating pattern. In some cases, it is contemplated that the first portion 182 may have a first uniform, repeating pattern while the second portion 184 has a second, different, uniform, repeating pattern. The braided reinforcement 180 also includes an intervening portion 186, located between the first portion 182 and the second portion 184, in which the individual filaments are not braided in a uniform, repeating pattern. Instead, the individual filaments have been moved to either side to form a void 188. In some cases, the individual filaments that have been moved to either side to form the void 188 may be considered as forming a first steerable strut 190 and a second steerable strut 192. The void 188 may be configured to accommodate drainage holes 22 formed therein. It will be appreciated that the first steerable strut 190 and the second steerable strut 192 may impact bending characteristics, and thus steerability, of any catheter or other device incorporating the braided reinforcement 180.

The braided reinforcement 180 may be formed using a braiding machine, such as those available commercially under the HERZOG® name. In some instances, it is contemplated that the braided reinforcement 180 may be braided onto an inner polymeric layer (such as the inner polymeric member 30), and then one or more additional polymeric layers such as but not limited to the polymeric outer sheath 50 may be disposed over the braided reinforcement 180 to form a drainage catheter. Accordingly, it is possible to form drainage catheters that are braid-reinforced, thereby providing drainage catheters with improved properties such as kink resistance and pushability while simultaneously enjoying relatively reduced wall thicknesses. This can mean a stronger catheter for a given diameter, or a smaller diameter catheter for a given kink resistance and pushability. This can mean a smaller outer diameter for a given lumen size, or a larger lumen size for a given outer diameter, for example. In some cases, the braided reinforcement 180 may instead be used to form any of a variety of different catheters and other devices.

Figure 10:
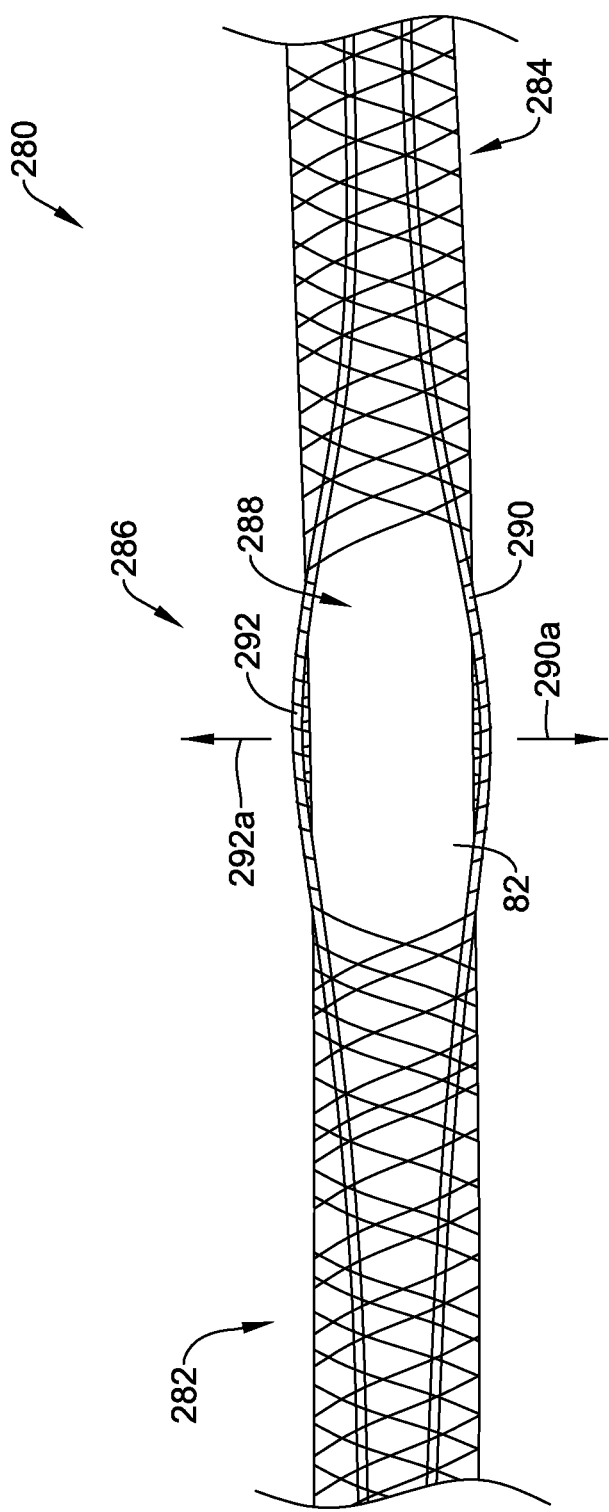
FIG. 10 is a side view of a braided reinforcement in accordance with an example of the disclosure.

FIG. 10 provides another example of a braided reinforcement 280. The braided reinforcement 280 includes a first portion 282 in which the individual filaments can be seen as being braided in a uniform, repeating pattern, and a second portion 284 in which the individual filaments can be seen as being braided in a uniform, repeating pattern. In some instances, the first portion 282 and the second portion 284 have the same uniform, repeating pattern. In some cases, it is contemplated that the first portion 282 may have a first uniform, repeating pattern while the second portion 284 has a second, different, uniform, repeating pattern. The braided reinforcement 280 also includes an intervening portion 286, located between the first portion 282 and the second portion 284, in which the individual filaments are not braided in a uniform, repeating pattern. Instead, the individual filaments have been moved to either side to form a void 288. In some cases, the braided reinforcement 280 includes a first axial strut 290 and a second axial strut 292. While two axial struts 290, 292 are illustrated, disposed on either side of the void 288, in some cases the braided reinforcement 280 may include three, four or more distinct axial struts.

The braided reinforcement 280 may be formed using a braiding machine, such as those available commercially under the HERZOG® name. In some instances, it is contemplated that the braided reinforcement 280 may be braided onto an inner polymeric layer (such as the inner polymeric member 30) or onto the mandrel 82, as shown. In some cases, the braided reinforcement 280 may be formed using a multi-step braiding process in which the individual filaments are braided together in a first braiding pattern to form the overall structure of the braided reinforcement 280, including the first portion 282, the second portion 284 and the intervening portion 286. A subsequent, different, braiding process may then form the axial struts 290, 292 in such a way as that the axial struts 290 and 292 are interwoven about the individual filaments forming the first portion 282, the second portion 284 and the intervening portion 286. In some instances, the first axial strut 290 and the second axial strut 292 may each be formed from a plurality of individual filaments. In some cases, the first axial strut 290 and the second axial strut 292 may instead be formed from heavier wires that are woven into the braided reinforcement 280. In some cases, the void 288 may be formed (or widened) by applying a radial force to each of the first axial strut 290 and the second axial strut 292, in directions indicated by arrows 290a and 290b, respectively.

One or more additional polymeric layers such as but not limited to the polymeric outer sheath 50 may be disposed over the braided reinforcement 280 to form a drainage catheter. Accordingly, it is possible to form drainage catheters that are braid-reinforced, thereby providing drainage catheters with improved properties such as kink resistance and pushability while simultaneously enjoying relatively reduced wall thicknesses. This can mean a stronger catheter for a given diameter, or a smaller diameter catheter for a given kink resistance and pushability. This can mean a smaller outer diameter for a given lumen size, or a larger lumen size for a given outer diameter, for example. In some cases, the braided reinforcement 280 may instead be used to form any of a variety of different catheters and other devices.

Figure 11:
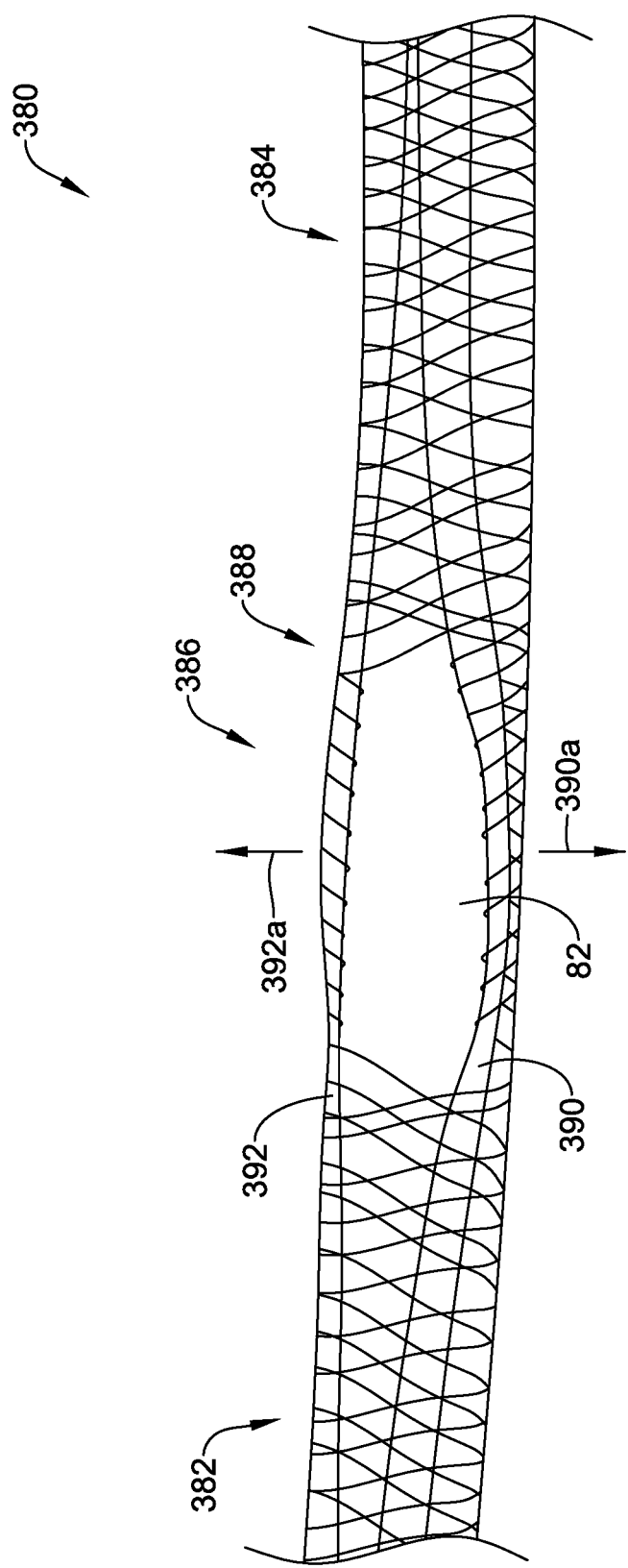
FIG. 11 is a side view of a braided reinforcement in accordance with an example of the disclosure.

FIG. 11 provides another example of a braided reinforcement 380. The braided reinforcement 380 includes a first portion 382 in which the individual filaments can be seen as being braided in a uniform, repeating pattern, and a second portion 384 in which the individual filaments can be seen as being braided in a uniform, repeating pattern. In some instances, the first portion 382 and the second portion 384 have the same uniform, repeating pattern. In some cases, it is contemplated that the first portion 382 may have a first uniform, repeating pattern while the second portion 384 has a second, different, uniform, repeating pattern. The braided reinforcement 380 also includes an intervening portion 386, located between the first portion 382 and the second portion 384, in which the individual filaments are not braided in a uniform, repeating pattern. Instead, the individual filaments have been moved to either side to form a void 388. In some cases, the braided reinforcement 380 includes a first axial ribbon 390 and a second axial ribbon 392. While two axial ribbons 390, 392 are illustrated, disposed on either side of the void 388, in some cases the braided reinforcement 280 may include three, four or more distinct axial struts.

The braided reinforcement 380 may be formed using a braiding machine, such as those available commercially under the HERZOG® name. In some instances, it is contemplated that the braided reinforcement 380 may be braided onto an inner polymeric layer (such as the inner polymeric member 30) or onto the mandrel 82, as shown. In some cases, the braided reinforcement 380 may be formed using a multi-step braiding process in which the individual filaments are braided together in a first braiding pattern to form the overall structure of the braided reinforcement 380, including the first portion 382, the second portion 384 and the intervening portion 386. A subsequent braiding process may extend the axial ribbons 390, 392 through the braided reinforcement 380. In some cases, the axial ribbons 390, 392 may be polymeric, although this is not required in all cases. In some cases, the void 388 may be formed (or widened) by applying a radial force to each of the first ribbon 390 and the second ribbon 392, in directions indicated by arrows 390a and 390b, respectively.

One or more additional polymeric layers such as but not limited to the polymeric outer sheath 50 may be disposed over the braided reinforcement 380 to form a drainage catheter. Accordingly, it is possible to form drainage catheters that are braid-reinforced, thereby providing drainage catheters with improved properties such as kink resistance and pushability while simultaneously enjoying relatively reduced wall thicknesses. This can mean a stronger catheter for a given diameter, or a smaller diameter catheter for a given kink resistance and pushability. This can mean a smaller outer diameter for a given lumen size, or a larger lumen size for a given outer diameter, for example. In some cases, the braided reinforcement 380 may instead be used to form any of a variety of different catheters and other devices.

The drainage catheter 10, as well as the various components thereof, may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In at least some embodiments, portions or all of the structures disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the drainage catheter 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of endoscope 10 or the various components thereof to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A catheter, comprising:
   an inner polymeric layer;
   a braided reinforcement disposed about the inner polymeric layer;
   the catheter including a first portion in which the braided reinforcement has a first filament pattern and a second portion in which the braided reinforcement has a second filament pattern different from the first filament pattern;
   an outer polymeric layer disposed about the braided reinforcement and including an outer surface;
   one or more drainage holes extending through the inner polymeric layer and the outer polymeric layer and disposed within the second portion of the catheter;
   a first axial strut extending axially along the catheter on a first side of the one or more drainage hole; and
   a second axial strut extending axially along the catheter on a second side of the one or more drainage hole;

wherein the first and second axial struts are each formed from wires heavier than wires forming the braided reinforcement.

2. The catheter of claim 1, wherein the second filament pattern is configured to enable the one or more drainage holes to pass through the braided reinforcement without cutting or breaking any of the filaments forming the braided reinforcement.

3. The catheter of claim 1, wherein the one or more drainage holes are disposed relative to the braided reinforcement such that each of the filaments extend intact from a position distal of the one or more drainage holes to a position proximal of the one or more drainage holes.

4. The catheter of claim 1, wherein the reinforcement braid is configured such that the second filament pattern of the reinforcement braid provides a region free of filaments in order to accommodate the one or more drainage holes.

5. The catheter of claim 4, wherein the reinforcement braid is braided to include the region free of filaments.

6. The catheter of claim 1, wherein the reinforcement braid comprises metal filaments.

7. The catheter of claim 1, wherein the reinforcement braid comprises polymeric filaments.

8. The catheter of claim 1, wherein the first filament pattern provides a uniform spacing between braid filaments.

9. The catheter of claim 1, wherein the second filament pattern provides a non-uniform spacing between braid filaments.

10. The catheter of claim 1, wherein the first and second axial struts are each formed from polymer ribbons.

11. A drainage catheter, comprising:
a polymeric tubular member;
a braided reinforcement disposed about the polymeric tubular member and including a repeating braid pattern extending over a first portion of a length of the drainage catheter;
the braided reinforcement including a modified braid pattern extending over a second portion of the length of the drainage catheter, the modified braid pattern providing a region without any braid filaments;
a drainage hole extending through the polymeric tubular member and disposed within the region without any braid filaments;
a first axial strut extending axially along the catheter on a first side of the drainage hole; and
a second axial strut extending axially along the catheter on a second side of the drainage hole;
wherein the first and second axial struts are each formed from a plurality of individual filaments.

12. The drainage catheter of claim 11, further comprising a polymeric sheath disposed over the braided reinforcement, the drainage hole extending through the polymeric sheath.

13. The drainage catheter of claim 11, wherein the modified braid pattern extends over less than about 25 percent of the length of the drainage catheter.

14. The drainage catheter of claim 11, wherein the modified braid pattern extends over less than about 10 percent of the length of the drainage catheter.

15. The drainage catheter of claim 11, wherein the braided reinforcement comprises stainless steel and/or tungsten.

16. The drainage catheter of claim 11, wherein the braided reinforcement comprises polyetheretherketone (PEEK) or high molecular weight polyethylene.

17. The drainage catheter of claim 11, wherein the braided reinforcement comprises a hybrid of metal filaments and polymer filaments.

18. A method of forming a drainage catheter including a braided reinforcement and a drainage hole, the method comprising:
braiding a braided reinforcement over a polymeric inner liner;
the braided reinforcement including a repeating braid pattern extending over a first portion of a length of the drainage catheter and a modified braid pattern extending over a second portion of the length of the drainage catheter, the modified braid pattern providing a region without any braid filaments;
interweaving first and second axial struts axially through the braided reinforcement such that the first axial strut extends on a first side of the region without any braid filaments and the second axial strut extends on a second side of the region without any braid filaments;
wherein the first and second axial struts are each formed from wires heavier than wires forming the braided reinforcement; or wherein the first and second axial struts are each formed from a plurality of individual filaments;
reflowing a polymeric outer sheath over the braided reinforcement; and
forming a drainage hole extending through the polymeric inner liner and the polymeric outer sheath, the drainage hole positioned within the region without any braid filaments.

19. The method of claim 18, wherein forming the drainage hole does not damage any of the braid filaments of the braided reinforcement.

20. The method of claim 18, wherein forming the drainage hole comprises drilling, milling, hole-punching, laser cutting or melting through the polymeric inner liner and the polymeric outer sheath.

21. The method of claim 18, wherein braiding the braided reinforcement comprises programming a braiding machine to produce the repeating braid pattern extending over a first portion of a length of the drainage catheter and a modified braid pattern extending over a second portion of the length of the drainage catheter.

22. The method of claim 18, wherein the region without any braid filaments is formed by applying a first radial force to the first axial strut in a first direction radially away from a longitudinal axis of the braided reinforcement and applying a second radial force to the second axial strut in a second direction opposite the first direction and radially away from the longitudinal axis.

* * * * *